United States Patent [19]

Downey, Jr.

[11] Patent Number: 5,439,595
[45] Date of Patent: Aug. 8, 1995

[54] WATER DECONTAMINATION METHOD USING PEROXIDE PHOTOLYSIS IONIZER

[76] Inventor: Wayne F. Downey, Jr., 4501 Eland Downe, Phoenixville, Pa. 19460

[21] Appl. No.: 111,988

[22] Filed: Aug. 25, 1993

[51] Int. Cl.$^6$ .......................... B01D 17/06; C02F 1/48
[52] U.S. Cl. ................... 210/748; 210/749; 210/758; 210/759; 422/21; 422/24
[58] Field of Search ............... 210/748, 758, 759, 760; 422/21, 24

[56] References Cited

U.S. PATENT DOCUMENTS

| | | | |
|---|---|---|---|
| 3,523,076 | 8/1970 | Goerz et al. | 210/748 |
| 3,551,091 | 12/1970 | Veloz | 21/102 |
| 3,894,236 | 7/1975 | Hazelrigg | 250/435 |
| 3,920,547 | 11/1975 | Garrison et al. | 210/748 |
| 3,926,556 | 12/1975 | Boucher | 422/21 |
| 4,141,830 | 2/1979 | Last | 210/748 |
| 4,179,616 | 12/1979 | Coviello et al. | 250/529 |
| 4,201,917 | 5/1980 | Graentzel | 250/431 |
| 4,274,970 | 6/1981 | Beitzel | 210/748 |
| 4,535,247 | 8/1985 | Kurtz | 250/436 |
| 4,818,392 | 4/1989 | Werner et al. | 210/195.3 |
| 4,849,114 | 7/1989 | Zeff et al. | 210/747 |
| 4,857,204 | 8/1989 | Joklik | 210/748 |
| 4,954,147 | 9/1990 | Galgon | 53/53 |
| 4,968,489 | 11/1990 | Peterson | 422/186.3 |
| 5,120,450 | 6/1992 | Stanley, Jr. | 210/748 |
| 5,126,111 | 6/1992 | Al-Ekabi et al. | 422/186.3 |
| 5,131,757 | 7/1992 | Smith | 366/165 |
| 5,174,904 | 12/1992 | Smith | 210/759 |
| 5,266,214 | 11/1993 | Safarzedeh-Amiri | 210/759 |

FOREIGN PATENT DOCUMENTS 4000369  7/1991  Germany ............... 210/748

OTHER PUBLICATIONS

Bob Becker, "Analysis of a Second Generation Enhanced Photo-Oxidation Process for the Destruction of Water Born Organic Contaminants", Oct. 1991, pp. 1–15.

Leon M. Dorfman, et al., "Reactivity of Hydroxyl in Radical Aqueous Solutions", 1973, pp. 1–59.

J. Hoigné, et al., "The Role of Hydroxyl Radical Reactions in Ozonization Processes in Aqueous Solutions", 1976, pp. 377–386.

Marugan Malaiyandi, et al., "Removal of Organics in Water Using Hydrogen Peroxide in Presence of Ultraviolet Light", 1980, pp. 1131–1135.

*Primary Examiner*—Wilbur Bascomb, Jr.
*Attorney, Agent, or Firm*—Robert C. Podwil; Reed Smith Shaw & McClay

[57] ABSTRACT

Apparatus and a method are disclosed for decontaminating water, using an ionizing reactor. Water contaminated by organic compounds is introduced into a chamber in which it is concurrently irradiated by microwave and an ultraviolet source to activate it by photolysis. The water is then introduced to a hydroxyl reactor chamber. An oxidizing reagent, such as hydrogen peroxide, is irradiated by subjecting it to the UV source and conducting it through the chamber, without mixing it with the water. The activated water and irradiated oxidizing reagent are then vectored to a locus at which they are mixed under UV from the source. The apparatus and method may be incorporated into a water treatment system employing existing contaminant extraction techniques, such as immiscible fluids separation and turbo-aspirated sparging.

6 Claims, 6 Drawing Sheets

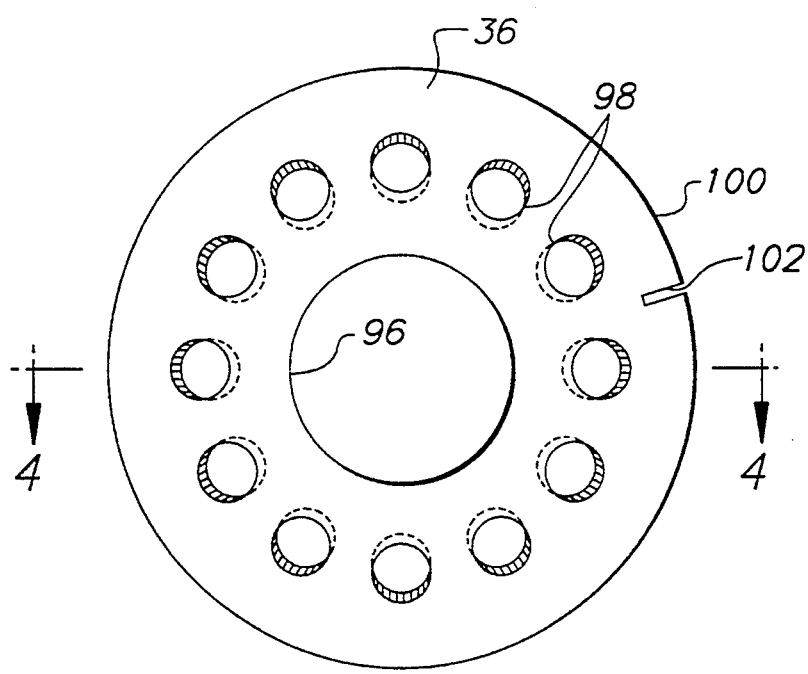
FIG. 3
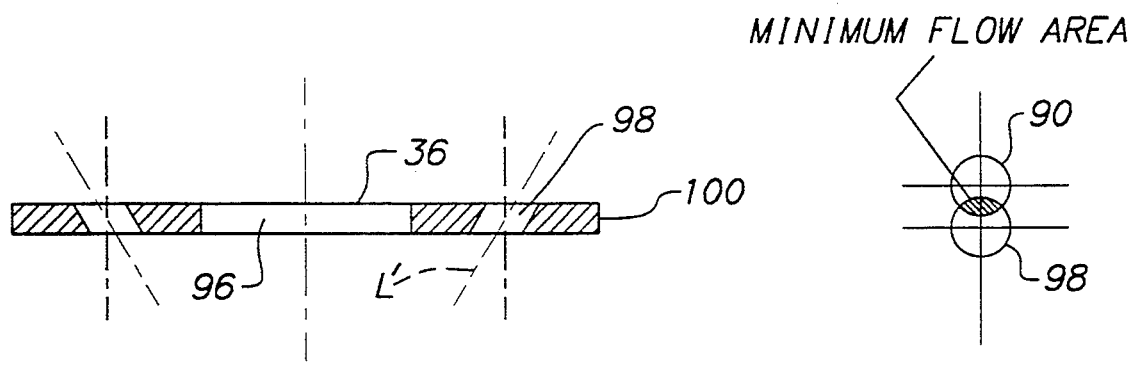
FIG. 4         FIG. 5
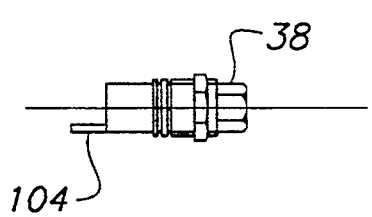      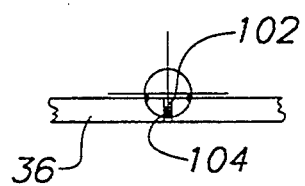
FIG. 6          FIG. 6a

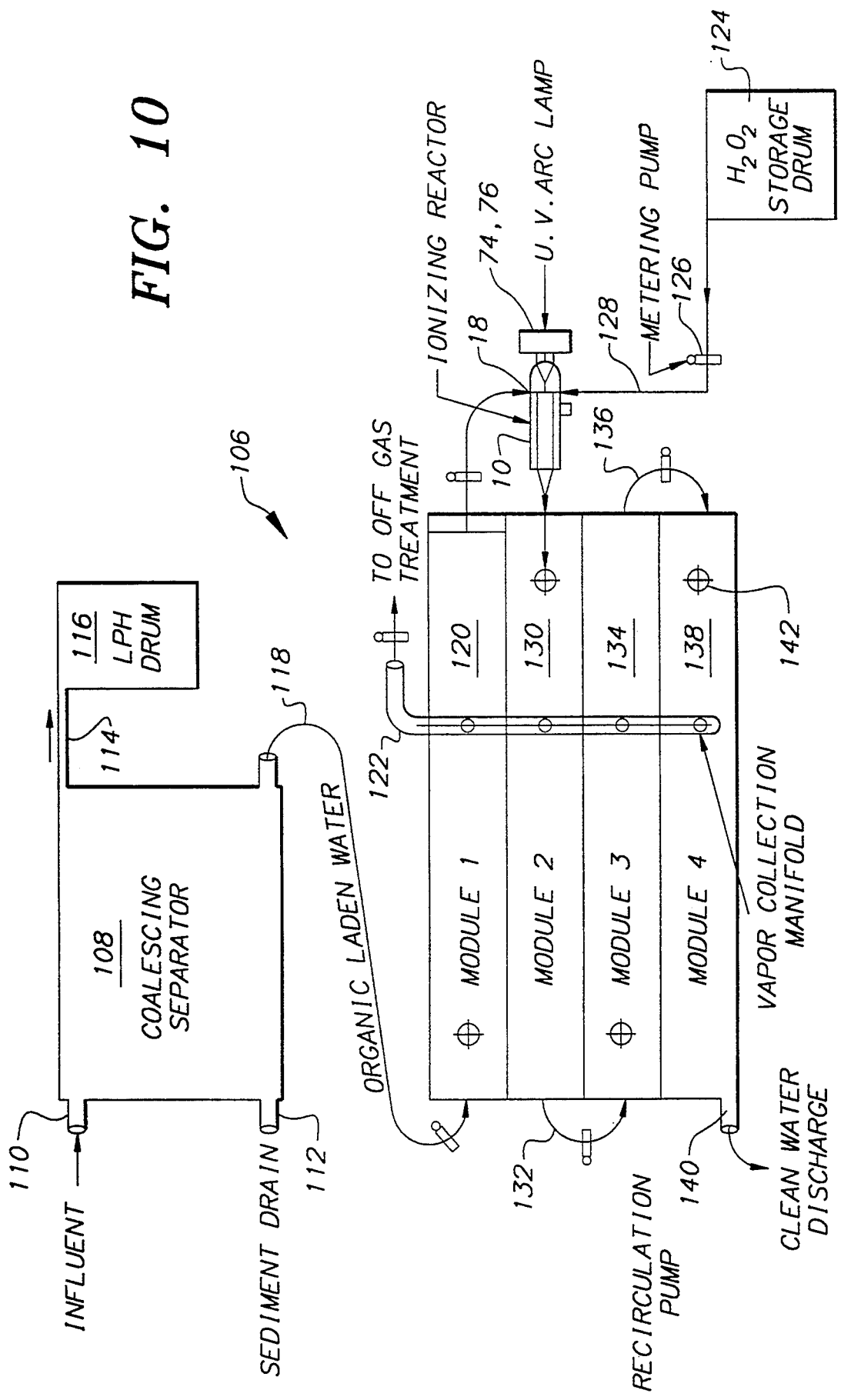

WATER DECONTAMINATION METHOD USING PEROXIDE PHOTOLYSIS IONIZER

BACKGROUND OF THE INVENTION

This invention relates to a water treatment method and an apparatus, and more particularly, to a method and apparatus for the removal from aqueous fluid of toxic and potentially hazardous organic compounds. The present method and apparatus exploit, synergistically, ultraviolet photolysis, the use of hydroxyl radicals, and microwave energy to, optimize the oxidation of organic contaminants in water.

The use of ultraviolet light and oxidants, such as ozone and hydrogen peroxide, to produce hydroxyl radicals, is well-known. Such a technique has been used to enhance oxidation of organic contaminants in industrial waste water, groundwater and other aqueous solutions. Direct photolysis of organic compounds by intense ultraviolet light is also well known and is used extensively in the water treatment industry. Microwave radiation (electromagnetic waves having a wavelength between about 0.3 and 30 centimeters) is commonly used to induce rapid heating of materials from within by oscillatory stimulation of hydrogen and nitrogen atoms within water and organic molecules. Oxidation of organic contaminants by ultraviolet light or by chemical reaction with hydrogen peroxide ultimately yields innocuous products: carbon dioxide, elemental carbon, water and oxygen.

It has now been found that exploitation of the above techniques in a single compact apparatus creates a potent oxidative water treatment method.

Existing apparatus and methods, using ultraviolet (UV) light and reagents such as hydrogen peroxide to create hydroxyl radicals, are able to treat substantial volumes of water, on the order of hundreds of gallons per minute. In "first generation" systems of this sort, it was proposed that low pressure UV discharge lamps be encased in quartz tubes immersed in tanks of water to be treated. Hydrogen peroxide was added to the water, and the mixture was allowed to flow around the submerged lamps. Problems with rapid fouling of the lamps and low production of hydroxyl radicals in such devices soon became apparent. Second generation apparatus of the above type incorporated manual cleaning mechanisms, and the use of polymer coatings (such as "Teflon" PTFE) on the quartz sleeve, additional oxidizers (such as ozone), and catalyzing additives (such as $TiO_2$) to enhance the rate of radical production. Lasers also have been used in efforts to increase energy transfer efficiency. Some efforts were successful to some extent, but at the price of significantly greater complexity and cost.

In known prior art apparatus and methods, the oxidizing reagent is added to the water prior to exposure of the mixture to the UV radiation. Since chemical oxidation is rapid, in such arrangements inorganic precipitates quickly form on the quartz sleeve or window surfaces, resulting in immediate and cumulative attenuation of the UV radiation.

Moreover, in known prior art apparatus and methods, addition of the oxidizing reagent to the water prior to UV exposure results in dilution of the reagent, so that the photon density of the UV radiation reaching the oxidant molecules is reduced by preferential absorption by the water, scattering and absorption by entrained particles in the water, and absorption by solutes. Sluggish mixing of the solution during irradiation also minimizes contact of the few radicals that are produced close to the light source, resulting in a relatively inefficient and certainly less than optimal capability for contaminant destruction.

The present invention provides a method and apparatus which addresses and obviates the above shortcomings of the prior art, by synergistically enhancing contaminant destruction by complementary techniques.

SUMMARY OF THE INVENTION

In one of its aspects, the present invention provides, for use in the treatment of waste water, an ionizing reactor for photochemically oxidizing organic compounds in aqueous solutions, using microwave-assisted photolysis and hydroxyl radical oxidation. The photolysis, production of hydroxyl radicals and the final hydroxylation reaction are all effected using a high pressure UV short arc lamp. Peroxide activation is made to take place in such a manner that a pure reagent is continuously irradiated, thus maximizing $O_3$ and $HO_2+$ and $OH+$ radical production. The reagent, thus activated, is injected into a downstream hydroxylation chamber, where it is mixed in a reaction zone with the pre-sensitized water, still under irradiation. The mixing is made to take place at a paraxial focus, where the ionization kinetics are most aggressive and the principal oxidative destruction of organic compounds occurs. The activated oxidizing reagent, containing free radicals, and the microwave and photosensitized water, are thus mixed vigorously at a point where incident concentrated deep UV radiation irradiates both fluids at once, to enhance the chemical degradation reaction.

Thus, a principal feature of a preferred embodiment of the invention is the simultaneous activation of pure oxidizing reagent with direct UV light and secondary photolysis and sensitization of contaminated water with UV radiation emitted from the walls of tubes (preferably of quartz) which carry the oxidizing reagent, and with microwave radiation from a microwave source (magnetron) positioned to direct high energy electromagnetic waves into the angular path of influent water circulating in a vortex around the tubes.

In its method aspect, the invention contemplates the use of a concentrated beam of deep spectrum ultraviolet light, which is manipulated using an optical array to simultaneously irradiate a reagent such as hydrogen peroxide and to irradiate out of fluid contact with the reagent (and preferably in an environment charged with microwave radiation) water to be treated. The water and the reagent are then mixed vigorously, under continued UV irradiation to optimize oxidation of waterborne contaminants.

A prime advantage of the above-described peroxide photolysis ionizer is that a maximum number of free radicals are produced using one UV source, which is itself safely and efficiently located separate from the reaction chamber. Presensitization of the water by photolysis enhances the ultimate reaction of the contaminants with the free radicals during subsequent hydroxylation.

Because the hydroxylation reaction occurs downstream from any light transmitting or reflecting surfaces, it does not contribute to precipitate fouling of those surfaces, a common problem in the prior art.

As indicated above, all of the fluid to be treated is preferably made to converge at a narrow vertex where a concentrated beam of UV light of optimal wavelength is directed. This minimizes the energy needed to generate free radicals while maximizing the treatment volume capability of the apparatus.

The present invention may be used to good advantage as part of a comprehensive water treatment system in an industrial setting requiring the removal and rapid destruction of recalcitrant contaminants from water, within a minimal space. In one of its embodiments, the present invention may be incorporated into a system comprising a coalescing separator for receiving waste water, a multi-stage turbo-aspiration unit, and one or more peroxide photolysis ionizers of the above-described type associated with the various stages of the turbo-aspiration unit. All of the above components, it has been found, can be mounted on the chassis of a small truck or trailer for portability.

BRIEF DESCRIPTION OF THE DRAWINGS

There are seen in the drawings forms of the invention which are presently preferred (and which constitute the best mode contemplated for carrying the invention into effect), but it should be understood that the invention is not limited to the precise arrangements and instrumentalities shown.

FIG. 3 is a plan view of a ringjet water flow control ring used in the invention;

FIG. 4 is a cross-sectional view of the ringjet water flow control ring shown in FIG. 3, taken along the line 4—4 in FIG. 3;

FIG. 5 is a diagrammatic detail view, illustrating the manner in which the ringjet water flow control ring controls the volume of water flow in apparatus in accordance with the invention;

FIG. 6 is a detail view, in side elevation, illustrating a vernier control element for the ringjet flow control ring;

FIG. 6a is an end elevation view of the vernier control depicted in FIG. 6, showing the manner in which the control element cooperates with the ringjet flow control ring.

FIG. 10 is a flow diagram of a water treatment system in accordance with the invention.

DETAILED DESCRIPTION OF THE INVENTION

Figure 1:
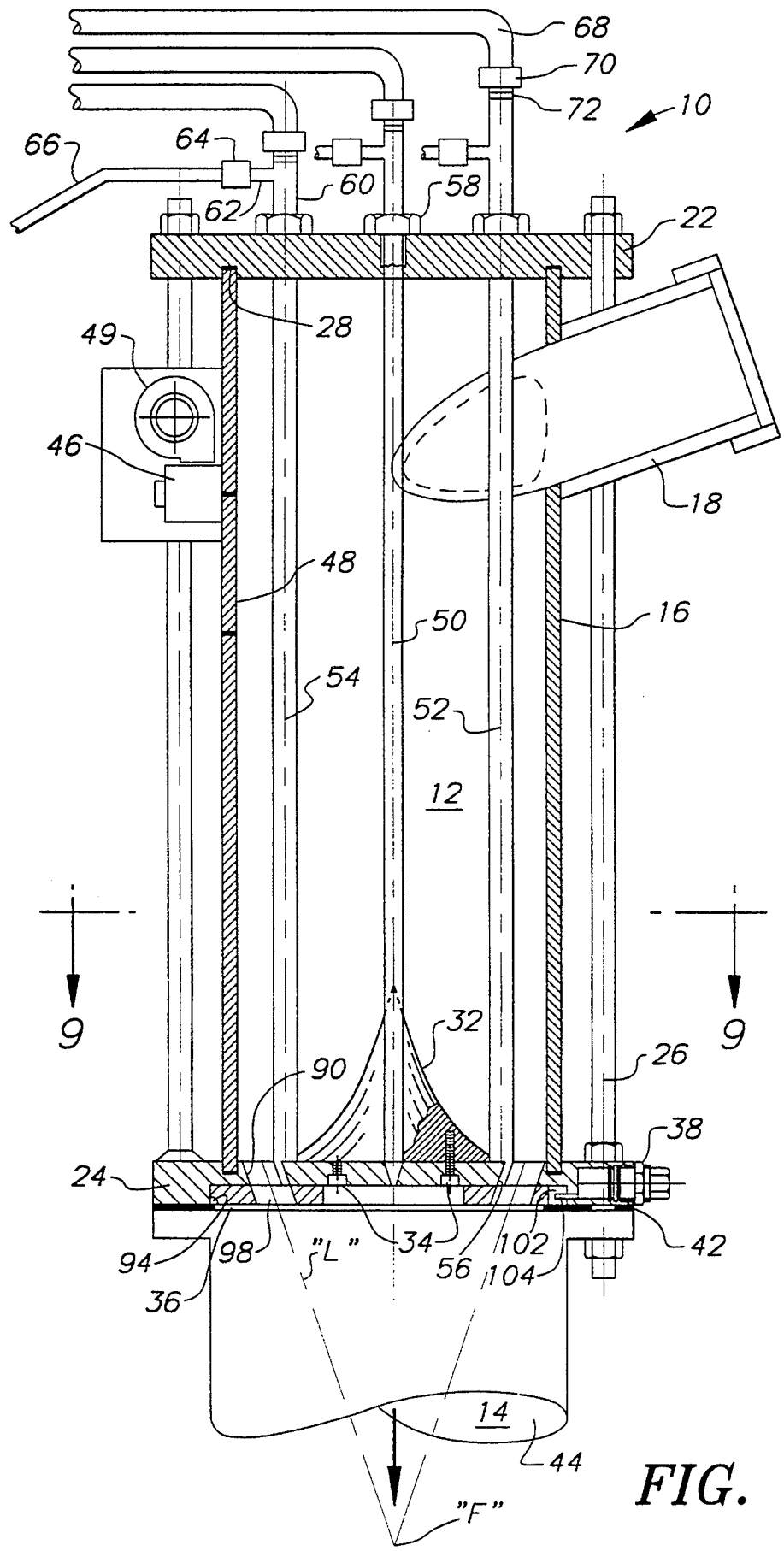
FIG. 1 is a side elevation view, in cross section, of a chamber assembly of the peroxide photolysis ionizer of the present invention.

Referring now to the drawings in detail, wherein like elements are designated by like reference numerals, there is seen in FIG. 1 an ionizing reactor, designated generally by the reference numeral 10. The reactor 10 comprises, in general, a photolysis chamber assembly, designated generally by the reference numeral 12, and a hydroxyl reactor chamber, designated generally by the reference numeral 14.

Figure 8:
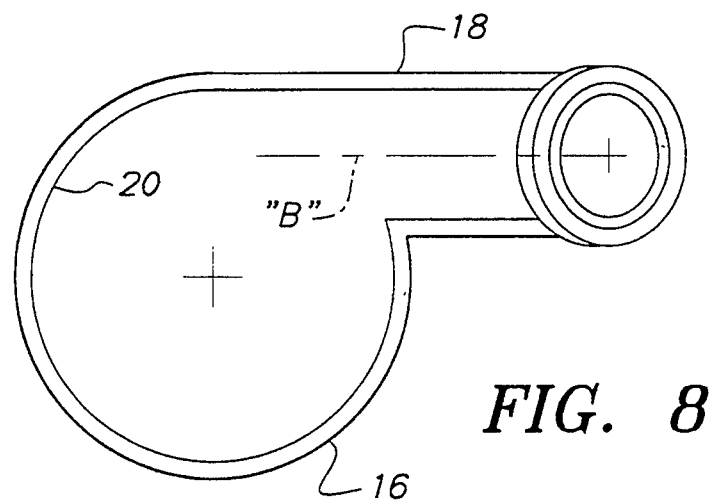
FIG. 8 is a top view of a photolysis chamber in accordance with the invention.
Figure 7:
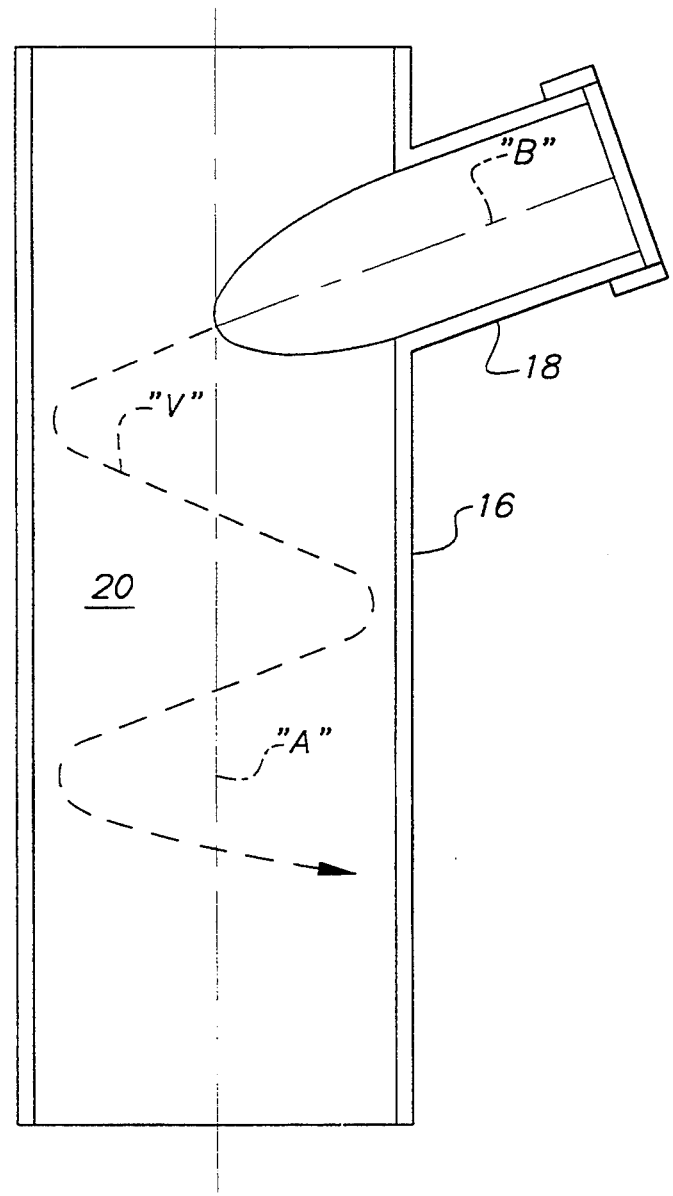
FIG. 7 is a side elevation view of a photolysis chamber in accordance with the invention.

Referring now to FIGS. 7 and 8 in addition to FIG. 1, the photolysis chamber assembly 12 consists, in the illustrated embodiment, of a generally elongated cylindrical shell 16, preferably of stainless steel. Associated with the shell 16 is a water injection port 18. As is perhaps best seen in FIGS. 7 and 8, the port 18 is so arranged and orientated with respect to the longitudinal axis "A" of the shell 16 that a stream of water flowing through the port 18 will impinge on the curved interior wall 20 of the shell 16 and assume a helical or volute path, designated diagrammatically in FIG. 7 as "V". Referring now to FIG. 8, it will be seen that in a transverse cross-sectional view, the port 18 enters tangentially with respect to the circular cross-section of the shell 16. Referring to FIG. 7, it will be seen that the longitudinal axis "B" of the water port 18 is oblique with respect to the axis "A" of the shell 16, thus encouraging development of the desired helical or volute flow of water within the shell 16.

Referring again to FIG. 1, the shell 16 is supported and retained by an end flange 22 (which may also be referred to as an "access flange", and a ringjet flange 24, which will be described in greater detail below. Suitable numbers of assembly rods 26 join the end flange 22 and ringjet flange 24 at locations around their respective peripheries. The rods 26 serve to retain respective ends of the shell 16 in peripheral seats 28 and 30 in the end flange 22 and ringjet flange 24, respectively.

Referring again to FIG. 1, associated with the ringjet flange 24 within the shell 16 when the photolysis chamber assembly 12 is assembled, is a hyperbolic reflector body 32, with a quadratic surface, shaped to direct radiation within the shell 16 for maximum effect. The reflector body 32 is preferably fabricated of highly polished aluminum, sputter-coated with sapphire to provide abrasion and corrosion protection and to optimize spectral reflectivity. Bolts 34 secure the reflector 32 to the ringjet flange 24.

Also associated with the ringjet flange 24 is a flow control ring 36 (seen in detail in FIG. 3 and 4 and described below), and a vernier control 38 (also discussed below) for the flow control ring 36.

Secured to the ringjet flange 24, as by bolts 40, is a tubular hydroxyl reactor chamber 14, which includes a water outlet port 44. A suitable gasket 42 is disposed between the reactor chamber 14 and the ringjet flange 24.

Other aspects of the ionizing reactor 10 will now be described in detail.

Associated with the shell 16, at a position generally juxtaposed to the water port 18, is a magnetron 46. The magnetron 46 is associated with a microwave-transparent "window" 48, which enables microwave radiation produced by the magnetron 46 to enter the shell 16 and impinge upon water entering the shell 16 through the port 18. A cooling fan 49 or other suitable cooling arrangement may be provided for the magnetron.

Figure 9:
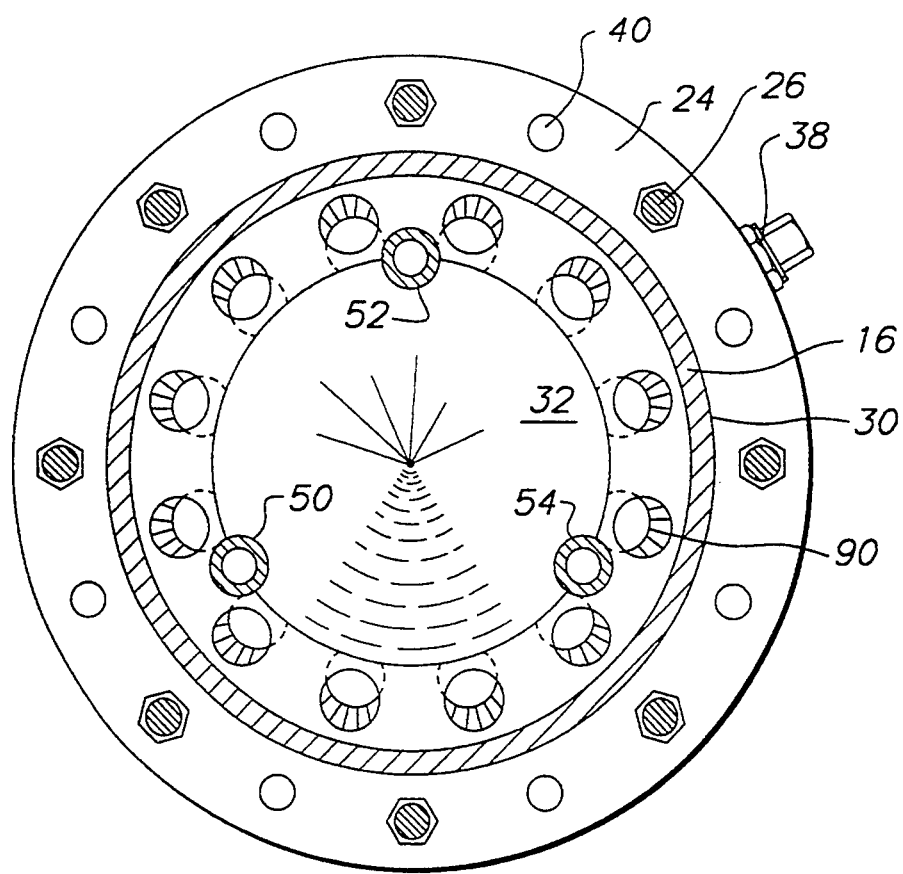
FIG. 9 is an end view, in cross-section, taken along the line 9—9 in FIG. 1.

Associated with the access flange 22 are quartz tubes 50, 52 and 54. The quartz tubes 50–54 extend, as is seen in FIGS. 1 and 9, into association with the ringjet flange 24, and include, in the vicinity of the ringjet flange 24, tapered nozzle ends 56. Jam nuts 58, with suitable gasket features, secure the upper ends of the quartz tubes 50–54 to the access flange 22. Associated with the upper ends of the quartz tubes 50–54 are T-fittings, of which the T-fitting 60 associated with the quartz tube 54 is typical. The T-fitting 60 provides an inlet 62 for reagent, as well as a coupling 64 to facilitate attachment of a reagent supply conduit 66. The quartz tubes 50–54 traverse the length of the photolysis chamber 12, in a direction parallel to the axis "A".

Also associated with the quartz tubes 50–54 are fiber optic sources, of which the illustrated source 68, a fiber optic conductor, may be considered typical. The fiber optic conductors 68 are coupled to the respective quartz tubes, such as the quartz tube 52, by fiber optic couplers, such as the coupler 70, and the upper ends of the quartz tubes 50–54 are sealed at the couplers by quartz windows, such as illustrated quartz window 72 associated with the tube 54. The conductors 68 are preferably of the high deep UV transmission fluid-filled type.

It will now be apparent that hydrogen peroxide introduced to the quartz tubes 50–54 through supply conduits, such as the conduit 66, will flow the length of the quartz tubes 50–54 and the photolysis chamber 12, to emerge at the nozzle ends 56 of the quartz tubes 50–54.

Figure 2:
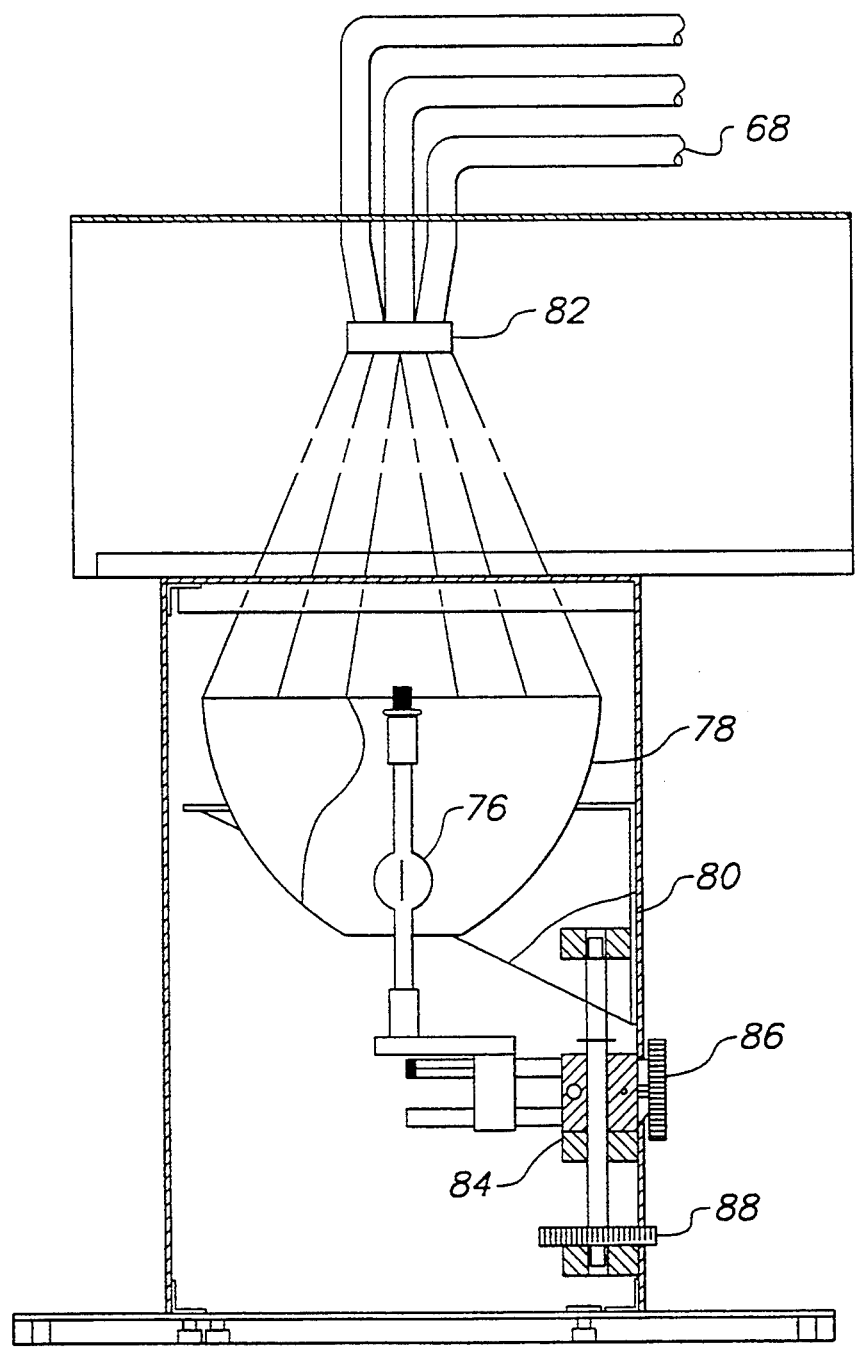
FIG. 2 is a front elevation view, in cross section, of an arc lamp and associated fiber optic transmission bundles for use in the present invention.

Referring now to FIG. 2, an exemplary ultraviolet source is seen. The illustrated source provides an arc lamp 76, disposed within an ellipsoidal reflector 78, both within a housing 80. A trifurcated optic collector 82 is juxtaposed to the reflector 78 and associated with respective ends of fiber optic conductors such as the above-described fiber optic conductor 68. It will be understood that each fiber optic conductor 68 is associated with one of the quartz tubes 50–54. A cross-slide mechanism 84, associated with the housing 80 and arc lamp 76, provides for focus and alignment adjustments for the arc lamp. Any suitable mechanism may be used for incremental adjustment of the position of the arc lamp 76. Suitable adjustment wheels or knobs 86 (for arc lamp alignment) and 88 (for focus) are provided. The arc lamp may be a 350 watt high pressure short arc mercury-xenon lamp, of the kind presently commercially available from Advanced Radiation Corp., Ushio Corp. and Ultra Violet Products, among others.

The application of UV radiation to the quartz tubes 50–54 in the above manner results in irradiation of the hydrogen peroxide flowing through the tubes 50–54, and, by Lambertian diffusion, irradiation of the photolysis chamber 12. The chamber 12 is preferably also simultaneously subjected to microwave radiation produced by the magnetron 46, so that water in the photolysis chamber 12 is irradiated and sensitized by the concurrent microwave and UV photon impingement. The peroxide reagent is continuously activated by direct UV radiation during its internal course along the length of the tubes 50–54. The reagent also serves as a light pipe, conducting UV radiation to the hydroxyl reactor chamber 14.

Referring now to FIGS. 3, 4 and 9, the manner in which activated reagent and sensitized water are directed to a paraxial focus point in the hydroxyl reactor chamber 14 (where conducted UV radiation traveling axially through the reagent also impinges on the fluids) which will now be described. It will be understood that the principal oxidation reaction produced by the reactor 10 occurs at this locus, and may be further enhanced by mixing in a downstream turbo-aspirated sparging apparatus, as will be described below.

Referring now to FIGS. 1, 3, 4 and 9, the ringjet flange 24 is provided with a circular array of water orifices 90 (twelve in the illustrated embodiment), extending through the ringjet flange at a preferred angle of 20° with respect to the longitudinal axis "A" of the hydroxyl reactor chamber 14. The illustrated orifices 90 are evenly distributed around the periphery of the ringjet flange 24, and at the same radial distance from the center of the ringjet flange. As is seen in FIG. 1, the respective longitudinal center lines "L" of the orifices 90 converge at a locus (or focal point) "F". The activated oxidizing reagent (hydrogen peroxide) emerging from the tubes 50–54 exits from the nozzle ends 56 into the hydroxyl reactor chamber 24 at the positions perhaps best seen in FIGS. 1 and 9. The reagent exits within the circle of the orifices 90, and into a zone adjacent the locus or focal point "F", where the activated oxidizing reagent containing free radicals and the microwaved and photosensitized water are mixed. The UV radiation conducted by the reagent in the quartz tubes 50–54 is likewise transmitted to the hydroxyl reactor chamber 14, where the incident concentrated radiation continues the irradiation of both fluids as mixing occurs.

The manner in which the rate of water flow between the photolysis chamber 12 and hydroxyl reactor chamber 14 may be controlled will now be described.

Referring to FIG. 1, the ringjet flange 24 has in one of its surfaces a circular recess 94. The flow control ring 36 is also circular, and has an outer diameter which allows it to be received in the recess 94. Referring to FIG. 5, the flow control ring 36 has a central clearance opening and an array of orifices 98, corresponding in number to the number of orifices 90 of the ringjet flange 24. The orifices 98 extend through the flow control ring 36 at an angle corresponding to the angle of the orifices 90 of the ring jet flange 24 (here 20°). The orifices 98 of the flow control ring 36 are disposed at the same radial distance from the center of the flow control ring 36, that distance being selected so that the orifices 98, when aligned with the orifices 90, form respective continuous passages of circular cross section.

Referring now to FIG. 3, it will be seen that the flow control ring 36 has a peripheral edge 100, interrupted at one point by a radially directed drive slot 102. Referring to FIG. 1, the vernier control 38 is mounted in the ringjet flange 24. The vernier control 38 has an eccentrically mounted drive pin 104, which projects into the drive slot 102 (as is perhaps best seen in FIGS. 1 and 6a). Rotation, therefore, of the vernier control 38 causes the drive pin 104 to rotate the flow control ring 36 relative to the ringjet flange as the pin 104 traverses the height of the slot 102. Rotation of the flow control ring 36 relative to the ringjet flange 24 causes offset of the orifices 90 and 98, as seen for example in FIG. 5, and consequent reduction of the flow area provided by the orifices. Thus, the total area of the orifices available for transfer of water between the chambers 12 and 14, and hence the flow volume and velocity, may be finely adjusted.

FIG. 10 illustrates a water treatment system in accordance with the invention, in which the above-ionizing reactor cooperates with a number of known components assembled in a unique manner, to provide efficient treatment of contaminated water. Referring now to FIG. 10, the system, designated generally by the reference numeral 106, includes a coalescing separator 108, into which influent is introduced at 110. Heavy sediments and immiscible fluids are mechanically separated from the influent and removed at the sediment drain 112. Lighter contaminants, such as hydrocarbons in the liquid phase, are drawn off at a conduit 114 to a collection and storage drum 116. The remaining water, still containing organic contaminants, is withdrawn from the separator 108 through the conduit 118, and pumped as input into a tubro-aspirated sparger 120. Off gas from the sparger is removed through a manifold 122, and the water output of the sparger is directed and pumped to the water inlet port 18 of an ionizing reactor 10. Oxidizing reagent, such as hydrogen peroxide, is provided to the reactor 10 from a storage drum 124, by means of a metering pump 126 and conduit 128.

The effluent from the ionizing reactor 10 is introduced into a second sparger 130, whose off gasses are drawn off into the manifold 122. The efflux from the sparger 130 is pumped through a conduit 132 to a third sparger 134 (also associated with the manifold 122), and from the third sparger 134 through a conduit 136 to a fourth sparger 138 (also associated with the manifold 122). Clean water is discharged from the sparger 138 at a conduit 140. An aspirator 142 may advantageously be associated with each sparger 120, 130, 134 and 138.

It will be appreciated that, although four spargers ( and thus four sparging stages ) are shown, the present invention may be used with other numbers of sparging stages. Various commercially available sparging units are suitable for use in the above-described system.

The present invention may be embodied in other specific forms without departing from its spirit or essential attributes. Accordingly, reference should be made to the appended claims, rather than the foregoing specification, as indicating the scope of the invention.

I claim:

1. A method for the removal of contaminants from water, comprising the steps of:
   a. providing a first and a second reaction chamber and a source of ultraviolet radiation operatively associated therewith;
   b. introducing into the first reaction chamber a stream of water;
   c. providing a stream of oxidizing reagent out of fluid contact with the stream of water;
   d. simultaneously subjecting the water and the oxidizing reagent to the ultraviolet radiation to irradiate them and hydrolyze the reagent;
   e. introducing the irradiated water and hydrolyzed reagent to the second reaction chamber; and
   f. mixing the water and the reagent in the second chamber while subjecting the water and the reagent to ultraviolet radiation from the source.

2. A method in accordance with claim 1, and the further step of:
   g. subjecting the water in the first reaction chamber to microwave radiation while conducting said step of subjecting the water and the oxidizing reagent to the ultraviolet radiation.

3. A method in accordance with claim 2, wherein said step b. is so conducted as to direct the stream of water into helical flow within the first reaction chamber.

4. A method in accordance with claim 2, wherein said step e. comprises the further step of:
   h. directing the water and the reagent to a focal zone.

5. A method in accordance with claim 1, wherein said step d. and said step f. comprise the further steps of:
   i. providing in the first chamber a plurality of light-conducting tubular members;
   j. so conducting said step c. that said stream of oxidizing reagent is made to flow through the tubular members; and
   k. conducting ultraviolet radiation from said source to respective ends of said tubular members, whereby scattering of ultraviolet radiation from said tubular members irradiates the water and the reagent in accordance with said step d., and radiation conducted by the tubular members and the reagent subjects the water and reagent in the second chamber to ultraviolet radiation from the source in accordance with said step f.

6. A method for the removal of contaminants from water, comprising the steps of:
   a. providing a first and a second reaction chamber and a source of ultraviolet radiation operatively associated therewith;
   b. introducing into the first reaction chamber a stream of water;
   c. providing a stream of oxidizing reagent and passing the stream of oxidizing reagent through the first reaction chamber out of fluid contact with the stream of water;
   d. simultaneously subjecting the water and the oxidizing reagent to the ultraviolet radiation to irradiate them and hydrolyze the reagent;
   e. introducing the irradiated water and hydrolyzed reagent to the second reaction chamber; and
   f. mixing the water and the reagent in the second chamber while subjecting the water and the reagent to ultraviolet radiation from the source.

* * * * *